(12) United States Patent
Young

(10) Patent No.: US 6,703,036 B1
(45) Date of Patent: Mar. 9, 2004

(54) STOMACH-ACTION MOLLUSCICIDES

(76) Inventor: Colin Leslie Young, 27 Reynolds Rd., Wattle Glen, Victoria, 3096 (AU)

( * ) Notice: Subject to any disclaimer, the term of this patent is extended or adjusted under 35 U.S.C. 154(b) by 0 days.

(21) Appl. No.: 09/554,434

(22) PCT Filed: Nov. 12, 1998

(86) PCT No.: PCT/AU98/00941

§ 371 (c)(1),
(2), (4) Date: May 15, 2000

(87) PCT Pub. No.: WO99/25194

PCT Pub. Date: May 27, 1999

(30) Foreign Application Priority Data

Nov. 14, 1997 (AU) .............................................. PP 0386

(51) Int. Cl.⁷ .............................................. A01N 25/08
(52) U.S. Cl. ........................ 424/410; 424/405; 424/406; 424/407; 424/408; 424/409; 424/421; 424/646; 424/647; 424/648; 424/84; 514/499; 514/502
(58) Field of Search ................................. 424/405–409, 424/84, 646–648, 410; 514/499, 502; 426/1

(56) References Cited

U.S. PATENT DOCUMENTS

| | | | | | |
|---|---|---|---|---|---|
| 2,836,537 | A | * | 5/1958 | Kaptaoon | 167/22 |
| 4,238,484 | A | * | 12/1980 | Stein et al. | 424/202 |
| 5,362,749 | A | * | 11/1994 | Henderson et al. | 514/492 |
| 5,437,870 | A | * | 8/1995 | Puritch et al. | 424/410 |
| 6,093,416 | A | * | 7/2000 | Young | 424/409 |

FOREIGN PATENT DOCUMENTS

| | | | |
|---|---|---|---|
| AU | 22526/88 | | 3/1989 |
| AU | 78623/91 | | 12/1991 |
| AU | 32232/95 | | 3/1996 |
| AU | 12970/97 | | 8/1997 |
| WO | 97/26789 | * | 7/1997 |

OTHER PUBLICATIONS

Maxicrop Multiguard –M505 p1–3, Feb. 1997.*
Australian Patent App. No. 689399 (12203/97) of Colin Leslie Young: vol. 1, Opposition thereto by W. Neudorff GmbH KG, Evidence in Support.

Australian Patent App. No. 689399 (12203/97) of Colin Leslie Young: vol. 2, Opposition thereto by W. Neudorff GmbH KG. Evidence in Support.

Australian Patent App. No. 689399 (12203/97) of Colin Leslie Young: vol. 3, Opposition thereto by W. Neudorff GmbH KG, Evidence in Answer.

Australian Patent App. No. 689399 (12203/97) of Colin Leslie Young: vol. 4, Opposition thereto by W. Neudorff GmbH KG, Evidence in Reply.

Australian Patent App. No. 689399 (12203/97) of Colin Leslie Young: vol. 5, Opposition thereto by Arthur Yates & Co. Limited, Evidence in Support.

Australian Patent App. No. 689399 (12203/97) of Colin Leslie Young: vol. 6, Opposition thereto by Arthur Yates & Co. Limited, Evidence in Support.

Australian Patent App. No. 689399 (12203/97) of Colin Leslie Young: vol. 7, Opposition thereto by Arthur Yates & Co. Limited, Evidence in Answer.

Australian Patent App. No. 689399 (12203/97) of Colin Leslie Young: vol. 8, Opposition thereto by Arthur Yates & Co. Limited, Evidence in Reply.

Australian Patent App. No. 689399 (12203/97) of Colin Leslie Young: vol. 9, Opposition thereto by Arthur Yates & Co. Limited and Opposition thereto by W. Neudorff GmbH KG, Further Evidence.

* cited by examiner

*Primary Examiner*—Neil S. Levy
(74) *Attorney, Agent, or Firm*—Burns, Doane, Swecker & Mathis, L.L.P.

(57) ABSTRACT

A stomach-action molluscicide, which includes a metal complexone and a suitable additive for enhancing the molluscicidal activity of the metal complexone. The additive may be selected from a surfactant or an additional source of ferric ions. Examples of the surfactant include sodium dodecyl sulphate or sorbitan monostearate, while an example of the additional source of ferric ions is ferric orthophosphate.

21 Claims, No Drawings

STOMACH-ACTION MOLLUSCICIDES

This application is a national stage application filed under 35 U.S.C. § 371 of PCT Application No. PCT/AU98/00941, filed Nov. 12, 1998.

FIELD OF THE INVENTION

The present invention relates to improved stomach-action molluscicides. stomach poisons or edible baits containing them and their use in killing, controlling and/or inactivating molluscs, in particular, slugs and snails. More particularly, the present invention relates to a stomach-action molluscicide containing at least one additive, which is specifically included to increase the efficacy of such a molluscicide and which lowers the cost of production of such a molluscicide.

BACKGROUND TO THE INVENTION

Slugs and snails are major pests of agriculture in many parts of the world. The ecologies of different types of molluscs, which can be either terrestrial or aquatic, are very different and they usually require different types of treatment. The snail species, *Cepaea hortensis, Theba pisana, Helix aspersa, Cernuella virgata* and *Achatina* spp and the slug species, *Deroceras reliculatum, Arion hortensis, Milar budapestensis* and *Limax maximus* are of particular interest as targets. The common garden snail, *Helix aspersa* and the grey field slug, *Deroceras reticulatum*, are common garden pests throughout Australia. On the other hand, there are groups of snails, which have been introduced into Australia in the twentieth century that are ever increasing in number. These are the white Italian snail, *Theba pisana,* and the vineyard or Mediterranean snail, *Cernuella virgata,* which both cause extensive crop damage.

Significant crop damage by molluscs also occurs in northern Europe, the Middle East, North and Central America, South East Asia, Japan and New Zealand. In many cases, the rise to pest status of the slug or snail in question is a consequence of change—either in distribution (as in the case of accidental or deliberate introductions) or in agricultural practice, where crops or systems of cultivation may enable populations to rise to pest levels. Slugs are a major agricultural pest which cause significant crop damage by burying themselves in the soil and then moving along into holes drilled for planting new crop seeds in. Once the seed has been placed in the drill holes, they eat the inside out of the new seed, thereby potentially destroying the whole planting.

Chemical methods (i.e. the use of molluscicides), involving the use of stomach poisons for the control of such pests, are well known. Molluscicides containing metaldehyde and methiocarb have been in use for some while. The use of metal complexes in stomach-action molluscicides was first proposed by Henderson et al. in "Aluminium(II) and Iron (III) complexes exhibiting molluscicidal activity," Australian Patent AU-B-22526/88. In one of their studies, these workers compared the relative toxicities of some aluminium and iron salts and chelates and their efficacies as stomach poisons, by injecting known amounts into the gut lumen of molluscs and they found that, in fact, the metal chelates were more toxic than their corresponding salts. Metal chelates were also first trialed by Henderson et al as contact-action poisons. In one particular study, Henderson used the metal chelate, FeEDTA, as the toxic agent, finding it just as effective as various salts of Fe(III). (Henderson, I. F. et al, in "A New Group of Molluscicidal Compounds," BCPC mono., (1989), 41, "Slugs and Snails in World Agriculture", pp 289–294 eds. Henderson, I. F., British Protection Council, Farnham, U. K.).

More recently, Puritch el al in "Ingestible Mollusc Poisons," International Patent Application No. WO 96/05728 claimed a terrestrial mollusc stomach poison containing, as the active ingredient, either ferric edetate or the ferric hydroxy-ethyl derivative of edetic acid. These workers have also shown that mixtures of iron salts such as ferric sulphate, ferric chloride or ferric nitrate when mixed together with disodium EDTA or EDTA, as such, are toxic to the slug species, *Deroceras reliculatum.*

The term "stomach-action molluscicide" is used herein in its broadest sense and includes a molluscicide, which is capable of being ingested into the stomach of the mollusc in an effective amount so as to kill and/or inactivate the mollusc.

The term "metal complexone" is used in its broadest sense and refers to a chelate of a metal with at least one ligand of the complexone type. The term "complexone" as used herein refers to an organic ligand containing at least one iminodiacetic group $—N(CH_2CO_2H)_2$, or two aminoacetic groups $—NHCH_2CO_2H_2$, or a derivative of either of these where the $—CH_2$ group is substituted, which form complexes with most cations. Suitable complexones include those disclosed in Wilkinson, G., "Comprehensive Coordination Chemistry," Volume 2, Chapter 20.3, pp 777–792 which is incorporated herein by reference.

In general, most toxic compounds are also repellent and the interaction of toxicity with repellency prevents the ingestion of sufficient poison to kill the mollusc. Therefore, the essential problem that an effective stomach-action molluscicide has to overcome is that of palatability since in order for it to be effective, it must be ingested by the mollusc. Although Puritch et al claimed that their formulations provide a palatable molluscicide, indeed tests carried out on these formulations by the present inventor revealed the acidic, and hence possibly unpalatable, nature of these formulations. It is believed that a significant proportion of the efficacy, claimed by Puritch et al, is possibly due to the molluscicidal formulation of either ferric edetate or the ferric hydroxy-ethyl derivative of edetic acid, or indeed, mixtures of iron salts, such as ferric sulphate, ferric chloride or ferric nitrate, when mixed together with disodium EDTA or EDTA, acting as a contact poison rather than an ingestible poison. It is further believed that the claimed palatable nature of these formulations arises not so much from the inclusion of the specific active ingredient, but rather from the elements of the "inert" carrier containing bran/flour and a phagostimulant, which would cause the bait to be sufficiently palatable to allow ingestion.

The present inventor therefore initially sought to develop a molluscicide, wherein the active ingredient itself was more palatable, efficacious and also one which was not harmful to the environment. In this, the present inventor was successful and developed and made an application for a patent, International Patent Application No: PCT/AU97/00033, for a stomach-action molluscicide, containing the hydroxy compound, $[Fe(OH)EDTA]^{2-}$ or its dimer, $[EDTA\text{-}Fe\text{—}O\text{—}Fe\text{-}EDTA]^{4-}$ as the active ingredient, which was found to be more palatable to molluscs and therefore also more efficacious.

The present inventor serendipitously discovered that the addition of $K_2CO_3$ or $CaCO_3$ as a filler to a molluscicidal bait containing FeEDTA, resulted in a bait that was more effective than with no additional filler being added. These fillers also fortuitously acted as pH adjusters which effectively adjusted the pH of the bait to around 8. At low pH, the Fe(III) atom in FeEDTA is surrounded by the two nitrogen atoms and the four oxygen atoms, provided by the hexadentate ligand, EDTA, and a water molecule acting as an additional seventh donor ligand. At a pH above 7, the water molecule is replaced by either an —OH group or an —O— group. At a pH of between 7 and 10, the species present in the majority are [Fe(III)(OH)EDTA]$^{2-}$ or its dimer, [EDTA-Fe—O—Fe-EDTA]$^{4-}$ with Fe(III)EDTA being present in the minority. The hydroxy compound and its dimer are in equilibrium, the relative amounts depending on the moisture of the pellet. According to F. G. Kari et al, Environ. Sci. Technol., (1995), 29, 1008, at a pH of about 8 to 8.5, there is virtually no Fe(III)EDTA present at all. The present inventor has found that molluscicides having a pH of greater than 7, but less than 9 or 10 appear to be more palatable than those having a pH of 7 or below. In addition, at higher pH, the Fe(III) ions are more readily replaced by Ca$^{2-}$ions, liberating the Fe(III) ions for passage through the intestinal epithelium into the blood stream. It is suggested that these Fe(III) ions may then complex with haemocyanin present as the oxygen-carrier in the blood of the mollusc, in some as yet unexplained way, resulting in an inhibition of the oxygen uptake by the mollusc, leading to its eventual death.

A further essential requirement for an efficacious stomach-action molluscicide is that premature termination of feeding must not result so that an insufficient amount of poison is ingested to kill the pest. In this way, the molluscicide needs to be more than a feeding deterrent or a crop protectant. One way of achieving this is to increase the concentration of active ingredient present in the bait. However, this leads to excessive costs of production and to a bait that is more harmful to non-target animals. This latter consideration is of particular concern since stomach-action poisons are often consumed by non-target organisms such as domestic animals, birds and children, particularly when baits are used. There is always a possibility that the bait will be consumed by such non-target organisms. Accordingly, the present invention seeks to improve the efficacy of the bait in such a way as to further decrease its harmful effects on non-target organisms.

Surprisingly, the present inventor has now found that the addition of surfactant to the molluscicidal formulation disclosed in International Patent No. PCT/AU97/00033 provides significant advantages over that formulation. Surfactants are principally known as agents, which reduce the surface tension of liquids and have been particularly widely used in the detergent industry. Surfactants have also been used in the molluscicidal industry, but principally for their emulsifying characteristics (Albright & Wilson, Patent No. GB 2 252 499 A, (1992)) and to facilitate the milling process of the molluscicide (Tavener et al, Patent No. AU91 178623). Henderson et al have shown that the efficacy of stomach-action molluscicides, containing metaldehyde and methiocarb, both highly toxic active ingredients, can be increased by the addition of small amounts of additives (Henderson et al, Ann. appl. Biol., (1992), 121, 423–430); (Bowen et al, Patent No. GB 2098 869 A, (1982) and Bowen et al, in BCPC Symposium Proceedings, (1996), 66, "Slug & Snail Pests in Agriculture," pp397–404).

A number of surfactants in the form of their aqueous solutions were claimed to have molluscicidal activity on aquatic snails. (Visser, S. A., Bull. Wld. Hlth. Org., (1965), 32, 713–719). Visser found that aqueous solutions of cationic detergents were on the whole more toxic than the anionic or non-ionic detergents used as aqueous solutions. Dawson et al, in BCPC Symposium Proceedings, (1996), 66, "Slug & Snail Pests in Agriculture," pp 439–444, eds. Henderson, I. F., British Protection Council, Farnham, U. K.) have investigated the repellency of a range of surfactants to the slug, *Deroceras reticulatum*. They found that in particular, tetraammonium salts were highly repellent and some polyphenylpolyethoxylates were also repellent with the degree of repellency varying with the degree of ethoxylation. These workers were interested in using surfactants as a repellent to crops. Their laboratory tests showed that crawling slugs rapidly detect and are deterred by topical applications of chemicals at low deposit rates. They concluded that surfactants were of limited use in this type of application, since they were rapidly removed from the plant by rain and by condensation.

Selected surfactants are considerably less toxic to mammals than others. Sodium dodecyl sulphate (SDS) is a surfactant, which is widely used as an emulsifier in agricultural chemicals. It is a popular choice amongst surfactants, since it is biodegradable and is generally regarded as being environmentally safe. Tseng et al, in Proceedings of the National Science Council, R. O. C., Part B: Life Sciences, Vol. 18, No. 3, (1994), pp 138–145, found that sodium dodecyl sulphate (SDS) was an effective molluscicide, when used on its own at a concentration of 100 ppm, for the semi-aquatic golden apple snail, *Pomacea canaliculata*. SDS was used in this case as an aqueous solution applied onto the water surface. Tseng et al also observed that snail movement and vital response stopped sooner at an acidic pH compared with at an alkaline pH. These workers believed that the molluscicidal activity of SDS appeared to be due to "dermal" absorption, rather than as an "oral" (stomach) poison.

However, although the use of surfactants have been studied in the past, the synergistic effects of surfactants with metal complexones in molluscicidal formulations or compositions have not been previously studied.

The present inventor found that several surfactants, tested under the experimental conditions leading to the present invention, exhibited no efficacy when used on their own on terrestrial molluscs. Accordingly, experiments were designed wherein the surfactant was employed in combination with a known stomach poison and it was found that a synergism exists between the metal complexone and the surfactant. The inclusion of surfactants as the synergistic additive in stomach-action poisons, in accordance with the present invention, offers considerable advantages over the presently known stomach-action molluscicides. Since it was believed that the surfactant would exhibit a synergistic effect with the metal chelate, its inclusion in the composition might enable the amount of metal chelate utilised in the composition of the bait to be reduced. Not only would this further reduce the harmful effects of the molluscicide on non-target organisms, but also, since less metal chelate would be required to produce the same level of efficacy, the inclusion of the surfactant might significantly lower the cost of production.

It is well known that the inclusion of the poison in a bait, as a pellet, gives significantly better results than the direct application of molluscicide lo the soil or application of the bait as a powder to the soil. Details of bait formulation in the prior art have generally been given without discussion of differences that might be expected from other formulations. Such differences are most probably significant in determining the amount of chelate required for effective control. Indeed, it is now believed by the present inventor that some of the ferric ions of the active ingredient, [EDTA-Fe—O—Fe-EDTA]$^{4-}$ actually react with the phytates or other natural chelating agents present in bran, a major component of the bait composition, making them unavailable for toxic action.

Investigations were consequently carried out as to the effect of the addition of an additional source of Fe(III) ions to the composition of the bait, with the belief that such addition would further increase the efficacy of the bait. A further consideration to this aspect of the present invention is the quality of the bran used in the composition. Fine, low-quality bran is relatively inexpensive, but use of this type of bran leads to a low rain-resistant pellet. On the other hand, extremely fine bran, known as "pasta bran," coupled with appropriate water-resistant additives can lead to a highly rain-resistant pellet. This latter alternative can be expensive and can, in fact, be more expensive than the total cost of all the other ingredients of the formulation. Since the amount of bran used in the formulation as a proportion of the total weight of the bait is considerable, the higher the percentage of bran, the higher the cost of production of the bait. It was believed that by increasing the amount of surfactant added, due to the synergistic effect, the amount of FeEDTA required might be lowered. As discussed above, since a percentage of added FeEDTA is removed from being available for molluscicidal activity by complexing with phytates or other natural chelators present in the bran, by lowering the amount of bran used, a higher percentage of FeEDTA is available for toxic action. Additionally, the cost of production would be lowered since the amount of bran is reduced. However, it was believed that a reduction in the amount of bran used might lower the attractiveness of the bait to the molluscs, since the bran is a major component affecting the palatability of the bait and therefore a balance between all these competing factors was required to be established.

Additional studies were therefore aimed at further lowering the amount of FeEDTA required for an effective kill rate and hence providing a molluscicide that was more cost effective to produce. Thus, experimental trials were designed where FeEDTA, in combination with an additional source of iron, were incorporated into the bait formulation.

Accordingly, it is an object of the present invention to combine the requirements of palatability of the molluscicide so that the poison is readily ingested, with the requirements of an effective amount of available Fe(III) ions, together with at least one additive that will increase the rate of absorption of the poison. It is also an object of the present invention to incorporate an additive, which complements and enhances the existing environmentally-friendly aspects of the use of the active ingredient, $[Fe(III)(OH)EDTA]^{2-}$ or in the form of its dimer, $[EDTA-Fe-O-Fe-EDTA]^{4-}$. In addition, the present invention provides a palatable, efficacious molluscicide, which is also less expensive to produce.

SUMMARY OF THE INVENTION

According to one aspect of the present invention, there is provided a stomach-action molluscicide including an effective amount of a metal complexone, an effective amount of at least one additive, excluding a metal carbonate, for enhancing the molluscicidal activity of the metal complexone, and a suitable non-liquid carrier therefor, wherein the metal of the metal complexone is selected from the group consisting of Group 2 metals, transition metals or Group 13 metals.

Preferably, the metal of the metal complexone is a transition metal. More preferably, the metal is selected from the group of iron(II) or iron(III), aluminium or copper. Most preferably, the metal is iron(III) or copper(II). Preferably, the complexone is ethylenediaminetetra-acetic acid or hydroxyethylethylenediaminetriacetic acid.

Preferably, the metal complexone is selected from the hydroxy-metal complexone, $[Fe(III)(OH)EDTA]^{2-}$, its dimer $[EDTA-Fe-O-Fe-EDTA]^{4-}$, or FeHEEDTA.

In a preferred form of the invention, the additive is a surfactant, wherein the surfactant is selected from the group of cationic, anionic or non-ionic surfactants. More preferably, the surfactant is anionic or non-ionic. Most preferably, the anionic surfactant is selected from the group comprising sodium dodecyl sulphate (SDS), calcium benzyl dodecyl sulphate (ALKANATE CS®) or ammonium dodecyl sulphate (ADS), but is in no way limited to these. Even more preferably, the surfactant is sodium dodecyl sulphate (SDS). When the surfactant is non-ionic, it is most preferably selected from the group of SPAN-type surfactants, comprising sorbitan monostearate and sorbitan monooleate.

Typically, the amount of surfactant required for efficacy is between about 0.05–1% of the weight of the molluscicide. Preferably, the amount is between about 0.1–0.4% by weight of the molluscicide. Most preferably, the amount is about 0.2% by weight of the molluscicide.

Typically, when used in combination with a surfactant, the amount of metal complexone required for efficacy is between about 3–7% by weight of the molluscicide. Preferably, the amount is between about 3–5% by weight of the molluscicide. Most preferably, the amount is about 3.5% by weight of the molluscicide.

In a preferred form of the invention, the non-liquid carrier for the metal complexone usually includes a mollusc food, such as a cereal, wheat flour, bran, arrowroot or rice flour, carrot, beer, rice hulls, comminuted cuttle fish, starch or gelatin, so that the mollusc is attracted to the edible bait. Non-nutrient carriers of interest include non-nutrient polymeric materials, pumice, carbon and materials useful as carriers for insecticides. The poison or bait may also contain other additives known in the art, such as mollusc phagostimulants, for example, sucrose or molasses; lubricants, such as calcium or magnesium stearate, talc or silica; binders which are suitably waterproof, such as paraffin wax, white oil or casein and flavouring agents such as BITREX® (a registered trade mark), which imparts a bitter taste and renders the poison or bait less attractive to non-target organisms and children. In order to inhibit deterioration of the poison or bait, preservatives such as sodium benzoate, vitamin E, alpha-tocopherol, 4-nitrophenol, ascorbic acid, methyl paraben, propyl paraben or sodium bisulfite may also be included.

Preferably, the waterproofing agent is selected from Guar gum, Lotus bean gum or a fatty acid alcohol. Typically, where the waterproofing agent is a fatty acid alcohol, this is present in an amount about between 1–5% by weight of the molluscicide. More preferably, the fatty acid alcohol is selected from the group of $C_{16}$–$C_{18}$ fatty acid alcohols. Most preferably, the $C_{16}$–$C_{18}$ fatty acid alcohols comprise about 2% by weight of the molluscicide and the $C_{16}$–$C_{18}$ fatty acid alcohol is HYDRENOL MY, which is a mixture of hexadecanol, heptadecanol and octadecanol.

To increase the density of the actual mixture before pelletising to reduce the airborne content and thus wastage of the mixture, a filler is added to the carrier. Preferably, the filler contains calcium or magnesium ions to assist in the replacement of iron in the metal complexone of the active ingredient. Typically, the filler is selected from $CaCO_3$, $K_2CO_3$, $MgCO_3$, or a combination of these, or $CaSO_4$, but is not limited to these. More preferably, the filler is a metal carbonate, which is present in a sufficient amount so that the pH is non-acidic. Typically, the poison or bait contains about 1–5 wt % of a metal carbonate as a filler. When the metal carbonate is $CaCO_3$, the preferred concentration is about 2–3% by weight of the molluscicide. When the metal carbonate is $K_2CO_3$, the preferred concentration is about 4–5% by weight of the molluscicide. When the metal carbonate is $MgCO_3$, the preferred concentration is about 0.5–5% by weight of the molluscicide.

Serendipitously, such a metal carbonate additionally acts as a pH adjustment agent and it was found that the efficacy of the molluscicide generally increased with an increase in pH up to a pH of about 10. At a pH of about 10, it was found that feeding was deterred. It was found, through trials which were carried out using various amounts of $CaCO_3$, $MgCO_3$ and $K_2CO_3$ combined, that a balance needs to be struck between the pH and the attractiveness of the bait to the molluscs. If the pH of the bait is too low, it has been found that the efficacy is significantly reduced. Preferably, the pH of the molluscicide is non-acidic. Typically, the molluscicide has a pH of about 7 and not exceeding 10. Preferably, the pH of the molluscicide is about 8. Preferably, the pH adjustment agent is $CaCO_3$ or $MgCO_3$. The amount of metal carbonate added largely depends on the other constituents present in the formulation. In general, a stomach poison having a neutral or alkaline pH, has proved to be more efficacious than one having an acidic pH. The $K_2CO_3$, $CaCO_3$ or $MgCO_3$ used as a filler and which adjusts the pH to about above 8, aids in the formation of the metal complexone, $[Fe(OH)EDTA]^{2-}$ or its dimer, $[EDTA-Fe—O—Fe-EDTA]^{4-}$. The relative amounts of each of the two different forms of the active ingredient will be determined by the amount of moisture present in the pellet.

According to another aspect of the invention, when the metal complexone is the hydroxy-metal complexone, $[Fe(III)(OH)EDTA]^{2-}$ or in the form of its dimer, $[EDTA-Fe—O—Fe-EDTA]^{4-}$, the molluscicide further includes additional Fe(III) ions added to the bait composition to ensure that an effective concentration of Fe(III) ions is present in the bait. Such addition of Fe(III) ions is to counteract the binding of Fe(III) with the phytates present in the bran or flour present in the carrier, thereby allowing maximum efficacy of the poison. Preferably, the additional Fe(III) ions are added in the form of a ferric salt or in the form of a clay to the composition of the bait. Typically, the clay employed is both one which contains a high concentration of Fe(III) and in the form which is suitable for use in the pelletiser. Preferably, the clay is a form of terracotta clay. More preferably, the clay is in the form of a powder.

Preferably, when the additional Fe(III) ions are added in the form of a ferric salt, the ferric salt is ferric orthophosphate. Typically, the amount of ferric orthophosphate required for efficacy is between about 1–5% by weight of the molluscicide. Preferably, the amount required is between about 1–3% by weight of the molluscicide.

Typically, when in combination with an effective amount of an additional source of iron and an effective amount of metal carbonate, the amount of metal complexone required for efficacy is between about 1–9% by weight of the molluscicide. Preferably, the amount is between about 2–3% by weight of the molluscicide. Most preferably, the amount is about 2.5% by weight of the molluscicide.

In a preferred embodiment, the additive is a surfactant in combination with an additional source of ferric ions. More preferably, the molluscicide includes a metal complexone, a surfactant, an additional source of ferric ions and a metal carbonate. Most preferably, the molluscicide includes an effective amount of FeEDTA, an effective amount of sodium dodecyl sulphate (SDS), an effective amount of ferric orthophosphate and an effective amount of calcium carbonate. Most preferably, the amount of FeEDTA is 2–3% of the weight of the molluscicide, the amount of SDS is about between 0.1–0.2% of the weight of the molluscicide, the amount of ferric orthophosphate is between about 1–2% of the weight of the molluscicide and the amount of calcium carbonate is between about 3–4% of the weight of the molluscicide.

The molluscicide is advantageously presented in a solid form such as tablets, a powder, granules or pellets. Those skilled in the art will appreciate that it is preferable to prepare the products, which are the subject of the invention, in a form that is easy for consumers to use. Pellets, for example, can be easily scattered from a box across the area to be protected. Preferably, the molluscicide is in the form of a pellet. More preferably, the pellet is between 1 and 4 mm long and less than 3 mm in diameter. Most preferably, the pellet is 1.5 mm long and 1.5–2.0 mm in diameter.

It is to be understood by those skilled in the art that the scope of the present invention includes the stomach-action molluscicide disclosed herein, when used in combination with at least one other molluscicide.

According to another aspect of the invention, the method of preparation of the stomach-action molluscicide in pellet form includes the steps of:

(i) blending the components together to form a blended composition;

(ii) heating the blended composition for about 1 to 5 minutes in the-presence of steam at an ambient temperature of between about 80° and 100° C.;

(iii) maintaining the composition at the ambient temperature between about 10 and 30 seconds; and (iv) forming the blended composition into one or more pellets.

Preferably, step (ii) is carried out at about 90° C. for about 2 minutes, whereafter step (iii) is carried out for about 15 seconds. Preferably, the blended composition is formed into pellets under pressure. Throughout this specification and the claims which follow, unless the context requires otherwise, the word "comprise," or variations such as "comprises" or "comprising," will be understood to imply the inclusion of a stated integer or group of integers but not to the exclusion of any other integer or group of integers.

EXAMPLES

The invention will now be illustrated with reference to the following non-limiting Examples:

There are many possible variables to consider when evaluating snail or slug pellets. Field trials are often poorly controlled and it is often difficult to arrive at unambiguous conclusions. It is possible to apply extensive statistical analysis to poorly designed or controlled experiments. However, a series of simple experiments in which variables are controlled lead to unambiguous conclusions with no need for statistical analysis. It was decided to compare the pellets under laboratory conditions which could closely mimic controlled field conditions, but would not present problems arising from incomplete collection and counting of dead specimens or non-uniform distribution of snails in the trial patches. No attempt was made to control the diurnal temperature or the length of daylight, even though it was known that these factors do play some part in snail and slug feeding activity but their role is minor compared with the effect of temperature.

In designing experiments to investigate the synergistic effects of surfactants with metal complexones in stomach-action poisons, it is necessary to consider at least the following variables:

(i) the bait formulation from the perspective of palatability;
(ii) the amount of surfactant used;
(iii) the concentration of the metal complexone used;
(iv) the species of mollusc upon which the molluscicide is to be effective; and
(v) the maximum daily temperature range over which the molluscicide must be effective.

The inventor had already concluded that there is a direct relationship between temperature and feeding in the consideration of the efficacy of metal complexone-based molluscicides. (Young, C. L., in "Metal chelates as stomach poison molluscicides for introduced pests, *Helix aspersa, Theba pisana, Cernuella virgata* and *Deroceras reticulatum* in Australia," BCPC mono., (1996), 66, "Slug and Snail Pests in Agriculture," eds. Henderson, I. F., British Protection Council, Farnham, U. K.). While the ideal feeding temperature for snails is around 20° C., the temperature should be about above 10° C. because at temperatures below this, feeding is considerably reduced. For *Helix aspersa,* under high humidity conditions the ideal feeding temperature is approximately 20°–25° C., whereas for *Deroceras reticulatum,* it appears to be considerably lower and probably about 15° C. in high humidity conditions.

For convenience in this experimental work, the snail species used were *Cochlicella barbara* and *Helix aspersa* and the slug species, *Deroceras reticulatum.* In the trials conducted, all snails could be accounted for, whereas a few of the slugs apparently disappeared. It is possible that the slugs died and decomposed but cannibalism could not be ruled out. Indeed, cannibalism in slugs has been reviewed (South, A., "Terrestrial Slugs: Biology, Ecology and Control," (1992), Ch. 11, Chapman & Hall, London) and the existence of cannibalism in slugs has been noted even in the presence of food. (Airey, W. J., "Laboratory studies on damage to potato tubers by slugs," in J. Mollusc. Stud., (1987), 53, 97–104).

Experiments were carried out in "plots," each "plot" consisting of a container of volume approximately 500 cm$^3$ and a total internal surface area of 300 cm$^1$. About ten small airholes, of 0.2 mm diameter, were made in the lid of each container. Fresh carrot slices or cabbage were used as an alternative food.

The metal complexone and the additive of the stomach poison are normally incorporated in a carrier, all three elements together constituting the molluscicidal bait. The non-liquid carrier of the present invention is based on wheat flour/bran and is typical of common carriers used in baits used throughout the world. Although the basic constituents of wheat flour/bran-based baits, as described by the present inventor in International Patent Application No. PCT/AU97/00023, are well-known in the industry, further experimentation for the purposes of the present invention was carried out.

Contrary to what appears to be commonly shared belief in the molluscicidal industry, the present inventor believes that the carrier is thought not to be inert, but rather that it binds the metal ions making them less available for effective molluscicidal activity. The reactive nature of phytates, which are natural chelating substances present in bran and wheat flour, is well known and extensively documented. A further aspect of the present invention therefore was to attempt to counteract the complexing of the Fe(III) ions with the phytates in the wheat flour and in the bran of the carrier. Consequently, investigations as to the lowest possible amount of bran in the formulation were carried out so as to further reduce the cost of production of the bait. The lower the amount of bran, the higher the concentration of active ferric ions that is available for molluscicidal activity i.e. the amount of metal complexone required to produce the same level of molluscicidal activity is reduced and, together with a lower amount of bran, these factors together lead to a lower cost of production. The addition of a surfactant, for example, to the formulation, which displays a synergistic effect with the metal complexone, further reduces the amount of metal complexone required to produce the same molluscicidal efficacy. Since the amount of surfactant needed to replace roughly 3% of metal complexone to give a similar efficacy is only 0.2% and the cost of surfactant is roughly equivalent to the metal complexone, the addition of surfactant to replace some of the metal complexone in the composition results in an overall lower cost of production.

Three different groups of trials were undertaken in order to clarify the relative influence of phytates in bran. These involved:
a) FeEDTA +sodium phytate;
b) FeEDTA +various proportions of bran; and
c) FeEDTA +various levels of iron from simple salts.

The surfactants used in the trials were specifically limited to be those which reinforce the environmental benefits of FeEDTA and the hydroxy derivative of FeEDTA, [Fe(OH)EDTA]$^{2-}$ or in the form of its dimer, [EDTA-Fe—O—Fe-EDTA]$^{2-}$. The toxicity, LD$_{50}$ values of several common surfactants for rat by oral administration are tabulated below for illustration purposes:

| Toxicity, LD$_{50}$ values of several common surfactants for rat by oral administration. | |
|---|---|
| Surfactant | LD$_{50}$ g/kg |
| Sodium dodecyl sulphate, SDS | 1.288 |
| Sorbitan monolaurate, (Span 20) | 33.6 |
| Sorbitan monostearate (Span 60) | 31 |
| PEG* 300 | 27.5 |
| PEG* 1500 | 44.2 |
| PEG* 4000 | 50 |
| PEG* 6000 | 60 |
| PEG* 1000 oleyl ether | 2.777 |
| PEG* monostearate | 44 |

*PEG is polyethylene glycol

In Example 1, the complexing effect of the phytates and other natural chelators present in flour was investigated. The following formulations were used:

| | |
|---|---|
| Formulation A | 2.50% FeEDTA + 0.868% dodecasodium phytate + Flour |
| Formulation B | 2.78% FeEDTA + 2.21% dodecasodium phytate + Flour |
| Formulation C | 2.67% FeEDTA + 0.587% ferric phosphate + Flour |
| Formulation D | 2.40% FeEDTA + 2.40% ferric phosphate + Flour |

Example 1

In this Example, the variety of snail used was *Helix aspersa* and the trial was carried out within a temperature range of 14–20° C. Six plots were used in the trial. The dead snails were removed and counted after 8 days. The results are shown in Table 1.

TABLE 1

Complexing effect of phytates and other natural chelators present in flour.

| Formulation | Kill Rate | % Kill Rate |
| --- | --- | --- |
| Control | 0/24 | 0% |
| Formulation A | 9/24 | 37% |
| Formulation B | 0/24 | 0% |
| Formulation C | 9/24 | 37% |
| Formulation D | 12/24 | 50% |

Summary

Comparing the results obtained for Formulations A and B, since in these formulations, the dodecasodium phytate simulates bran, it can readily be seen that with a lower amount of bran in the bait, the bait is more effective. Comparing the results obtained for Formulations C and D, the more additional ferric ions added, the more effective the bait, since the phytates and other natural chelating agents in the flour complex with and therefore effectively remove some of the ferric ions from being available for molluscicidal activity. The lower the amount of bran, the higher the concentration of ferric ions available for molluscicidal activity and therefore the greater the efficacy of the molluscicide. This experiment clearly shows that phytates in the flour and bran lock up ferric ions present in the bait and effectively limit their availability for efficacy.

In Examples 2 and 3, the efficacies of various surfactants in combination with FeEDTA and the hydroxy derivative [Fe(OH)EDTA]$^{2-}$ were trialed and compared to FeEDTA used on its own. The various surfactants trialed were as follows:

Teric N40—an ethylene oxide derivative of nonyl phenol made by ICI
Sodium dodecyl sulphate
Ammonium dodecyl sulphate
ALKANATE CS®—Calcium benzyl dodecyl sulphate in butanol made by ICI
ATPLUS®-3001A—a polyethyleneglycol surfactant made by ICI
Teric 200—an alkylene oxide derivative of an alkyl phenol made by ICI In Examples 2 and 3, the following formulations were used:

| | |
| --- | --- |
| Formulation E | 1.83% FeEDTA + 0.214% Teric N40 + Flour |
| Formulation F | 2.60% FeEDTA + 0.556% Teric N40 + Flour |
| Formulation G | 3.53% FeEDTA + 0.192% Teric N40 + Flour |
| Formulation H | 3.59% FeEDTA + 0.294% Teric N40 + Flour |
| Formulation I | 4.44% FeEDTA + 0.366% Teric N40 + Flour |
| Formulation J | 0.75% FeEDTA + 0.152% SDS + Flour |
| Formulation K | 1.18% FeEDTA + 0.131% SDS + Flour |
| Formulation L | 1.93% FeEDTA + 0.147% SDS + Flour |
| Formulation M | 2.93% FeEDTA + 0.147% SDS + Flour |
| Formulation N | 3.00% FeEDTA + 0.182% SDS + Flour |
| Formulation O | 4.80% FeEDTA + 0.138% SDS + Flour |
| Formulation P | 5.50% FeEDTA + 0.197% SDS + Flour |
| Formulation Q | 0.95% FeEDTA + 0.157% ADS + Flour |
| Formulation R | 1.41% FeEDTA + 0.336% ADS + Flour |
| Formulation S | 1.49% FeEDTA + 0.273% ADS + Flour |
| Formulation T | 2.95% FeEDTA + 0.665% ALKANATE CS ® + Flour |
| Formulation U | 2.85% FeEDTA + 0.50% ATPLUS ® + Flour |
| Formulation V | 2.86% FeEDTA + 0.233% Teric 200 + Flour |
| Formulation W | 3.70% [EDTA-Fe—O—Fe-EDTA] + 0.12% SDS + Bran/Flour |
| Formulation 1 | 0.42% FeEDTA + Flour |
| Formulation 2 | 0.86% FeEDTA + Flour |
| Formulation 3 | 1.52% FeEDTA + Flour |
| Formulation 4 | 3.80% FeEDTA + Flour |
| Formulation 5 | 4.70% FeEDTA + Flour |
| Formulation 6 | 6.50% FeEDTA + Flour |
| Formulation 7 | 7.70% FeEDTA + Flour |

Example 2

In this Example, the variety of snail employed was *Cochlicella barbara*. The trial was conducted within a temperature range of 9–18° C. The dead snails were removed and counted after 8 days. The results are shown in Table 2.

TABLE 2

Comparison of the efficacies of various formulations containing Teric N40 or SDS as surfactants in combination with FeEDTA.

| Formulation | Kill Rate | % Kill Rate |
| --- | --- | --- |
| Control | 0/30 | 0% |
| Formulation E | 20/30 | 67% |
| Formulation F | 19/30 | 63% |
| Formulation G | 24/30 | 80% |
| Formulation H | 24/30 | 80% |
| Formulation I | 20/30 | 67% |
| Formulation J | 19/30 | 63% |
| Formulation K | 19/30 | 63% |
| Formulation L | 25/30 | 83% |
| Formulation M | 27/30 | 90% |
| Formulation N | 26/30 | 87% |
| Formulation O | 20/30 | 93% |
| Formulation P | 27/30 | 90% |

Example 3

In this Example, the variety of snail employed was *Helix aspersa*. The trial was conducted within a temperature range of 14–20° C. The dead snails were removed and counted after 8 days. The results are shown in Table 3.

TABLE 3

Comparison of the efficacies of various formulations containing ADS, ALKANATE CS ®, ATPLUS ®, Teric 200 or SDS as surfactants in combination with FeEDTA or the oxo-dimer, [EDTA-Fe—O—Fe-EDTA]$^+$.

| Formulation | Kill Rate | % Kill Rate |
| --- | --- | --- |
| Control | 0/24 | 0% |
| Formulation Q | 1/24 | 4% |
| Formulation R | 6/24 | 25% |
| Formulation S | 4/24 | 17% |
| Formulation T | 13/24 | 54% |
| Formulation U | 7/24 | 29% |
| Formulation V | 7/24 | 29% |
| Formulation W | 15/24 | 62% |
| Formulation 1 | 0/24 | 0% |
| Formulation 2 | 0/24 | 0% |
| Formulation 3 | 0/24 | 0% |
| Formulation 4 | 9/24 | 37% |
| Formulation 5 | 12/24 | 50% |
| Formulation 6 | 20/24 | 83% |
| Formulation 7 | 15/24 | 62% |

Summary

The results from Examples 2 and 3 show that a formulation containing surfactant in combination with FeEDTA is generally more effective than one containing FeEDTA on its own at a similar concentration. For example, a comparison of Formulations 3, 4 and 5 with Formulations E, F, G, L and N clearly show the enhancement of toxic action by the addition of surfactant to FeEDTA.

In Example 4, the efficacies of various surfactants in combination with FeEDTA were trialed and compared to FeEDTA when used on its own. The following surfactants were trialed although SDS would be less preferred than the SPAN surfactants, sorbitan monostearate and sorbitan monooleate, due to its increased toxic nature (Refer to the Table of $LD_{50}$ values above):

SDS—sodium dodecyl sulphate
Sorbitan monostearate
Sorbitan monooleate
Cetyltrimethylarmmonium bromide
The various formulations used were as follows:

| Formulation 8 | 3.4% FeEDTA + Flour |
|---|---|
| Formulation 9 | 3.4% FeEDTA + 0.228% SDS + Flour |
| Formulation 10 | 3.4% FeEDTA + 0.50% SDS + Flour |
| Formulation 11 | 2.2% FeEDTA + Flour |
| Formulation 12 | 2.2% FeEDTA + 0.227% sorbitan monostearate + Flour |
| Formulation 13 | 2.2% FeEDTA + 0.279% sorbitan monooleate + Flour |
| Formulation 14 | 2.2% FeEDTA + 0.401% sorbitan monooleate + Flour |
| Formulation 15 | 2.2% FeEDTA + 0.76% sorbitan monooleate + Flour |
| Formulation 16 | 2.2% FeEDTA + 0.61% cetyltrimethylammonium bromide + Flour |

Example 4

In this Example, the variety of snail employed was *Helix aspersa*. The pellets used in the trial all contained FeEDTA with varying amounts of surfactant added. The trial was conducted within a temperature range of 17–28° C. The dead snails were removed and counted after 8 days. The results are shown in Table 4.

TABLE 4

Comparison of the efficacies of various formulations containing different amounts of surfactant in combination with FeEDTA.

| Formulation | Kill Rate | % Kill Rate |
|---|---|---|
| Control | 0/24 | 0% |
| Formulation 8 | 11/24 | 46% |
| Formulation 9 | 18/24 | 75% |
| Formulation 10 | 13/24 | 54% |
| Formulation 11 | 5/24 | 21% |
| Formulation 12 | 15/24 | 63% |
| Formulation 13 | 15/24 | 63% |
| Formulation 14 | 8/24 | 33% |
| Formulation 15 | 11/24 | 46% |
| Formulation 16 | 3/24 | 12% |

Summary

The results for Formulations 12 and 13 show that the efficacy of sorbitan monosterate is virtually equivalent to that of sorbitan monooleate. Also, the results from using Formulations 9 and Formulations 13, 14 and 15 show that the efficacy is very dependent on the amount of surfactant added. The addition of too much surfactant could result in a bait that is unpalatable. It can also be seen that the use of cetyltrimethylammonium bromide, a cationic surfactant, in the formulation resulted in a reduction of the efficacy. This is believed to be due to it being repulsive to molluscs and hence unpalatable.

In Example 5, the effect of the addition of varying amounts of clay to the bait containing the active ingredient in the form of the oxo-dimer, $[EDTA\text{-}Fe\text{—}O\text{—}Fe\text{-}EDTA]^{4-}$ was trialed and compared to the bait formulation containing no clay. This trial was both an investigation into the variation of the efficacy of the pellet with the hardness of the pellet and to investigate whether the terracotta-type clay utilized which contains a higher proportion of Fe(III) ions than most other clays, could provide the additional Fe(III) required by bran-containing baits.

The various formulations used were as follows:

| Formulation 17 | 5.07% [EDTA-Fe—O—Fe-EDTA] + Flour/bran |
|---|---|
| Formulation 18 | 4.90% [EDTA-Fe—O—Fe-EDTA] + 3.3% Clay + Flour/bran |
| Formulation 19 | 4.60% [EDTA-Fe—O—Fe-EDTA] + 8.7% Clay + Flour/bran |
| Formulation 20 | 4.20% [EDTA-Fe—O—Fe-EDTA] + 17.7% Clay + Flour/bran |
| Formulation 21 | 4.37% [EDTA-Fe—O—Fe-EDTA] + 13.8% bentonite* + Flour/bran |

*Bentonite is a clay-type material, which is used as a binder in stock feeds.

Example 5

In this Example, the formulations were trialed on three types of molluscs, the slug *Deroceras reticulatum* and the snails, *Cochlicella barbara* and *Helix aspersa*. The trial was conducted within a temperature range of 12–17° C. for *Deroceras reticulatum*, 9–18° C. for *Cochlicella barbara* and 12–17° C. for *Helix aspersa*. The dead snails were removed and counted after 8 days. The results are shown in Table 5.

TABLE 5

Comparison of the efficacies of various formulations containing different amounts of clay in combination with FeEDTA.

| Formulation | Deroceras reticulatum | % | Cochlicella barbara | % | Helix aspersa | % |
|---|---|---|---|---|---|---|
| Formulation 17 | 14/15 | 93% | 26/30 | 86% | 8/15 | 53% |
| Formulation 18 | 14/15 | 93% | 26/30 | 86% | 8/15 | 53% |
| Formulation 19 | 14/15 | 93% | 22/30 | 73% | 9/15 | 60% |
| Formulation 20 | 15/15 | 100% | | | 9/15 | 60% |
| Formulation 21 | | | | | 8/24 | 33% |

Summary

It can be seen from the above results that slugs are considerably easier to kill than snails. It has been found that, generally, snails require a higher concentration of active ingredient and a greater sophistication in the design of the formulation used for efficacious results. From the above, it can also be seen that the addition of a clay containing available Fe(III) ions can allow for a reduction in the amount of metal complexone required to obtain the same degree of efficacy.

In Examples 6 to 9, various formulations containing FeEDTA with and without $FePO_4$ and $MgCO_3$ were compared. All bait formulations were based on a flour:bran weight ratio of 2:1.

The various formulations used were as follows:

| Formulation 22 | 2.3% FeEDTA |
|---|---|
| Formulation 23 | 2.6% FeEDTA + 5.7% $CaCO_3$ |

-continued

| | |
|---|---|
| Formulation 24 | 2.2% FeEDTA + 20.1% CaCO$_3$ |
| Formulation 25 | 2.6% FeEDTA + 4.36% MgCO$_3$ |
| Formulation 26 | 2.3% FeEDTA + 0.88% FePO$_4$ + 0.62% MgCO$_3$ |
| Formulation 27 | 2.3% FeEDTA + 1.21% FePO$_4$ + 1.13% MgCO$_3$ |
| Formulation 28 | 2.3% FeEDTA + 1.86% FePO$_4$ + 0.93% MgCO$_3$ |
| Formulation 29 | 2.5% FeEDTA + 2.40% FePO$_4$ + 1.32% MgCO$_3$ |
| Formulation 30 | 2.4% FeEDTA + 2.19% FePO$_4$ + 2.69% MgCO$_3$ |
| Formulation 31 | 2.6% FeEDTA + 3.50% FePO$_4$ + 3.00% CaCO$_3$ |

Example 6

In this Example, the following formulations were trialed on *Helix aspersa*. The feed was carrot. The trial was conducted within a temperature range of 12–17° C. for *Helix aspersa*. The dead snails were removed and counted after 9 days. The results are shown in Table 6. The pH of each of the formulations was determined and is also presented in Table 6.

TABLE 6

Comparison of the efficacies of various formulations containing FeEDTA with and without additional iron phosphate and magnesium or calcium carbonate.

| | Formulation | | | | | | | |
|---|---|---|---|---|---|---|---|---|
| | #1 | #2 | #3 | #4 | #5 | #6 | Total | pH |
| Formulation 22 | 1/2 | 0/2 | 0/2 | 1/2 | 0/2 | 0/2 | 2/12 | 6.2 |
| Formulation 23 | 1/6 | 3/6 | 4/6 | 4/6 | | | 12/24* | 7.3 |
| Formulation 24 | 2/2 | 2/2 | 1/2 | 1/2 | 2/2 | 1/2 | 9/12 | 7.4 |
| Formulation 25 | 2/6 | 2/6 | 1/6 | 2/6 | | | 7/24* | 8.3 |

*number of dead snails after 10 days, plot sizes approximately three times standard i.e. 1.5 L and total internal surface area 900 cm$^3$.

Summary

Comparison of Formulation 22 with Formulations 23, 24 and 25 illustrates that the addition of calcium or magnesium carbonate enhances the kill rate. It is believed that this enhancement is due both to a change in pH and the ease with which the iron is replaced by either the calcium or magnesium ions in the active ingredient. The results from these examples suggest that calcium ions are more effective at enhancing the kill rate than magnesium ions.

Example 7

In this Example, the following formulations were trialed on *Helix aspersa*. The feed was carrot. The trial was conducted within a temperature range of 12–17° C. for *Helix asperse*. The dead snails were removed and counted after 7 days. The results are shown in Table 7.

TABLE 7

Comparison of the efficacies of various formulations containing FeEDTA with and without additional iron phosphate and calcium or magnesium carbonate.

| | Formulation | | | | | | |
|---|---|---|---|---|---|---|---|
| | #1 | #2 | #3 | #4 | #5 | #6 | Total |
| Formulation 22 | 1/2 | 0/2 | 0/2 | 1/2 | 0/2 | 0/2 | 2/12 |
| Formulation 26 | 1/2 | 0/2 | 1/2 | 1/2 | 1/2 | 1/2 | 5/12 |
| Formulation 27 | 2/6 | 4/6 | 3/6 | 2/6 | | | 11/24* |
| Formulation 28 | 1/2 | 0/2 | 1/2 | 1/2 | 1/2 | 1/2 | 5/12 |

TABLE 7-continued

Comparison of the efficacies of various formulations containing FeEDTA with and without additional iron phosphate and calcium or magnesium carbonate.

| | Formulation | | | | | | |
|---|---|---|---|---|---|---|---|
| | #1 | #2 | #3 | #4 | #5 | #6 | Total |
| Formulation 29 | 5/6 | 2/6 | 3/6 | 3/6 | | | 13/24* |
| Formulation 30 | 3/6 | 2/6 | 1/6 | 3/6 | | | 9/24* |
| Formulation 31 | 2/6 | 4/6 | 3/6 | 2/6 | | | 11/24* |

*number of snails dead after 10 days, plot sizes approximately three times standard i.e. 1.5 L and total internal surface area 900 cm$^3$.

Summary

Comparison between Formulation 22 and Formulations 26 to 31 illustrates that the addition of iron orthophosphate together with magnesium carbonate enhances the kill rate.

Example 8

In this Example, the following formulations were trialed on *Helix aspersa*:

| | |
|---|---|
| Formulation 32 | 5.17% CuEDTA + 5.73% CaCO$_3$ |
| Formulation 33 | 5.17% CuEDTA + 5.73% CaCO$_3$ + 0.24% SDS |

The feed was carrot. The trial was conducted within a temperature range of 12–17° C. for *Helix aspersa*. The dead snails were removed and counted after 6 days. The results are shown in Table 8.

TABLE 8

Comparison of the efficacies of various formulations containing CuEDTA and CaCO$_3$ with and without surfactant.

| | Formulation | | | | |
|---|---|---|---|---|---|
| | #1 | #2 | #3 | #4 | Total |
| Formulation 32 | 2/6 | 1/6 | 1/6 | 0/6 | 4/24 |
| Formulation 33 | 1/6 | 4/6 | 3/6 | 2/6 | 10/24 |

Summary

Comparison of Formulation 32 with Formulation 33 illustrates that the addition of surfactant more than doubles the kill rate.

Example 9

In this Example, the following formulations containing ferric hydroxyethylethylenediaminetriacetic acid were trialed on *Helix aspersa*:

| | |
|---|---|
| Formulation 34 | 3.36% FeHEEDTA |
| Formulation 35 | 2.99% FeHEEDTA + 11.1% CaCO$_3$ |

The feed was carrot. The trial was conducted within a temperature range of 12–17° C. for *Helix aspersa*. The dead snails were removed and counted after 6 days. The results are shown in Table 9.

TABLE 9

Comparison of the efficacies of various formulations containing FeHEEDTA and CaCO$_3$.

| | Formulation | | | | |
|---|---|---|---|---|---|
| | #1 | #2 | #3 | #4 | Total |
| Formulation 34 | 1/6 | 2/6 | 3/6 | 1/6 | 7/24 |
| Formulation 35 | 2/6 | 5/6 | 3/6 | 2/6 | 12/24 |

Summary

Comparison of Formulation 34 with Formulation 35 illustrates that the addition of calcium carbonate significantly enhances the kill rate.

Example 10

In this Example, the following formulations were trialed on *Helix aspersa*.

| Formulation 36 | 2.0% FeEDTA + 1.9% FePO$_4$ + 0.18% SDS + 3.6% CaCO$_3$ |
|---|---|
| Formulation 37 | 2.6% FeEDTA + 3.50% FePO$_4$ + 3.00% CaCO$_3$ |
| Formulation 38 | 2.3% FeEDTA |

The daily temperature range was 1 8–28° C. and the dead snails were removed and counted after 4 days. The results are shown in Table 10.

TABLE 10

Comparison of the efficacies of various combinations of FeEDTA, with or without a surfactant, an additional source of Fe(III) ions or CaCO$_3$.

| | Formulation | | | | | | |
|---|---|---|---|---|---|---|---|
| | #1 | #2 | #3 | #4 | #5 | #6 | Total |
| Formulation 36 | 1/3 | 1/3 | 2/3 | 2/3 | 3/3 | 1/3 | 10/18 |
| Formulation 37 | 1/3 | 2/3 | 0/3 | 1/3 | 2/3 | 0/3 | 6/18 |
| Formulation 38 | 1/3 | 0/3 | 2/3 | 0/3 | 0/3 | 1/3 | 4/18 |

Summary

Comparison of Formulation 36 with Formulation 37 illustrates that the addition of surfactant markedly enhances the kill rate. Comparison of Formulations 36 and 37 with Formulation 38 illustrates that the presence of additives, including a surfactant and an additional source of ferric ions, together with calcium carbonate, which raises the pH of the formulation, significantly enhance the kill rate.

Overall Summary

The results illustrate the variability in the kill rate obtained by the addition of surfactant, by an additional source of Fe(III), such as ferric orthophosphate and by a metal carbonate to the metal complexone in the bait composition. It is believed that the mechanism of action of the surfactants is that they increase the rate of the absorption of the Fe(III) ions allowing them to pass rapidly through the intestinal epithelium and so into the blood stream of the mollusc leading to its death. It is believed that the enhancement in efficacy obtained on the addition of ferric orthophosphate is that the latter complexes with the phytates present in the flour, thereby allowing the Fe(III) ions of the FeEDTA to take part in the molluscicidal activity, whilst the part played by the metal carbonate is that of a pH adjustment agent, which makes the bait more palatable and therefore increases the amount of poison ingested. The presence of calcium ions is also believed to aid in the release of ferric ions from the metal complexone to enable them to take part in molluscicidal activity.

The effect of all of these additives on the molluscicidal efficacy of the bait composition, containing a metal complexone as the active ingredient, has been clearly shown. The results illustrate that there are optimal amounts of the respective additive and the complexone that must be reached to achieve the highest kill rates. The variation in the amount of bran used proportionally to the amount of Fe(III) ions used and the effect this variable has on the efficacy of the bait has also been illustrated. In general, the higher the concentration of available Fe(III) ions in the bait formulation, the higher the resulting kill rate. In addition, the more palatable the bait, the higher the likelihood of the bait being ingested and therefore the greater the efficacy of the bait as a stomach-action molluscicide. In addition, the present invention has also illustrated the way in which the various additives can be used to reduce the amount of FeEDTA required to achieve optimum kill rates, thereby reducing the cost of producing an effective environmentally-acceptable stomach-action molluscicide.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification (unless specifically excluded) individually or collectively, and any and all combinations of any two or more of said steps or features.

What is claimed is:

1. A stomach-action molluscicide including an effective amount of a metal complexone of ethylenediaminetetraacetic add (EDTA) or hydroxyethylethylenediaminetriacetic acid (HEEDTA), an effective amount of at least one additive, excluding a metal carbonate, for enhancing the molluscicidal activity of the metal complexone, wherein said additive is a surfactant, an additional source of ferric ions, or a combination thereof, and a non-liquid carrier for the metal complexone and additive components of the molluscicide, wherein the metal complexone is [Fe(III)(OH)EDTA]$^{2-}$, the dimer [EDTA-Fe—OFe-EDTA]$^{4-}$, or FeHEEDTA, and wherein the amount of metal complexone is between about 1–7% of the weight of the molluscicide.

2. A stomach-action molluscicide according to claim 1, wherein the additive is a surfactant.

3. A stomach-action molluscicide according to claim 2, wherein the surfactant is selected from the group consisting of cationic, anionic and non-ionic surfactants.

4. A stomach-action molluscicide according to claim 3, wherein the anionic surfactant comprises sodium dodecyl sulphate (SDS), calcium benzyl dodecyl sulphate (ALKANATE CS®), or ammonium dodecyl sulphate (ADS).

5. A stomach-action molluscicide according to claim 4 wherein the surfactant is sodium dodecyl sulphate (SDS).

6. A stomach-action molluscicide according to claim 3, wherein the non-ionic surfactant is sorbitan monostearate or sorbitan monooleate.

7. A stomach-action molluscicide according to claim 2, wherein the amount of surfactant is between about 0.05–1% of the weight of the molluscicide.

8. A stomach-action molluscicide according to claim 1, wherein the additive is an additional source of ferric ions.

9. A stomach-action molluscicide according to claim 8, wherein the source of ferric ions is selected from a ferric salt or a clay.

10. A stomach-action molluscicide according to claim 9, wherein the ferric salt is ferric orthophosphate.

11. A stomach-action molluscicide according to claim 10, wherein the amount of ferric orthophosphate is between about 1–5% of the weight of the molluscicide.

12. A stomach-action molluscicide according to claim 1, wherein the additive is a surfactant in combination with an additional source of ferric ions.

13. A stomach-action molluscicide according to claim 12, wherein the additional source of ferric ions is ferric orthophosphate.

14. A stomach-action molluscicide according to claim 1, wherein the non-liquid carrier for the metal complexone includes a mollusc food, a mollusc phagostimulant, a waterproofing agent, a flavouring agent, a preservative, a filler, a lubricant and an effective amount of a pH adjustment agent.

15. A stomach-action molluscicide according to claim 14, wherein the pH adjustment agent is $CaCO_3$, $K_2CO_3$, or $MgCO_3$, or a combination of these, or $CaSO_4$.

16. A stomach-action molluscicide according to claim 14, wherein the amount of the pH adjustment agent is between about 1–5% of the weight of the molluscicide.

17. A stomach-action molluscicide according to claim 16, wherein the pH of the molluscicide is non-acidic when added to water.

18. A stomach-action molluscicide according to claim 17, wherein the pH is between about 7 and 10 when added to water.

19. A stomach-action molluscicide according to claim 18, wherein the pH is about 8 when added to water.

20. A stomach-action molluscicide according to claim 1, wherein the amount of metal complexone is between about 2–3% of the weight of the molluscicide.

21. A stomach-action molluscicide according to claim 1, wherein the metal complexone comprises a metal complexone in combination with at least one other molluscicide.

* * * * *

UNITED STATES PATENT AND TRADEMARK OFFICE
CERTIFICATE OF CORRECTION

PATENT NO. : 6,703,036 B1
DATED : March 9, 2004
INVENTOR(S) : Colin Leslie Young It is certified that error appears in the above-identified patent and that said Letters Patent is hereby corrected as shown below:

Column 18,
Line 34, should read -- ethylenediaminetetra-acetic acid -- instead of "ethylenediaminetra-acetic add".

Signed and Sealed this

Twenty-eighth Day of September, 2004

JON W. DUDAS
*Director of the United States Patent and Trademark Office*